United States Patent
Blann et al.

(10) Patent No.: US 7,297,832 B2
(45) Date of Patent: *Nov. 20, 2007

(54) TETRAMERIZATION OF OLEFINS

(75) Inventors: Kevin Blann, Alberton (ZA); Annette Bollmann, Henley-on-Klip (ZA); John Thomas Dixon, Vanderbijlpark (ZA); Arno Neveling, Sasolburg (ZA); David Hedley Morgan, Sasolburg (ZA); Hulisani Maumela, Johannesburg (ZA); Esna Killian, Vanderbijlpark (ZA); Fiona Millicent Hess, Sasolburg (ZA); Stefanus Otto, Sasolburg (ZA); Matthew James Overett, Johannesburg (ZA); Michael James Green, Johannesburg (ZA)

(73) Assignee: Sasol Technology (PTY) Limited, Johannesburg (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 10/539,237

(22) PCT Filed: Dec. 19, 2003

(86) PCT No.: PCT/ZA03/00186

§ 371 (c)(1),
(2), (4) Date: Feb. 10, 2006

(87) PCT Pub. No.: WO2004/056478

PCT Pub. Date: Jul. 8, 2004

(65) Prior Publication Data

US 2006/0173226 A1    Aug. 3, 2006

Related U.S. Application Data

(60) Provisional application No. 60/509,309, filed on Oct. 6, 2003, provisional application No. 60/478,379, filed on Jun. 13, 2003, provisional application No. 60/435,405, filed on Dec. 20, 2002.

(30) Foreign Application Priority Data

| Dec. 20, 2002 | (ZA) | ................... 02/10339 |
| Jun. 13, 2003 | (ZA) | ................... 03/4632 |
| Oct. 6, 2003 | (ZA) | ................... 03/7774 |

(51) Int. Cl.
C07C 2/08    (2006.01)
C07C 2/36    (2006.01)
C07C 2/32    (2006.01)
B01J 31/18    (2006.01)
B01J 31/24    (2006.01)

(52) U.S. Cl. ............. 585/527; 585/513; 585/514; 585/516; 502/102; 502/121; 502/124; 502/125

(58) Field of Classification Search ............... 585/514, 585/527, 513, 516; 502/103, 121, 124, 125
See application file for complete search history.

(56) References Cited

U.S. PATENT DOCUMENTS 2,699,457 A    1/1955    Ziegler et al.
4,628,138 A    12/1986    Barnett et al.

FOREIGN PATENT DOCUMENTS

WO    WO 02/04119 A1    1/2002

OTHER PUBLICATIONS

Carter et al.; "High Activity Ethylene Trimerisation Catalysts Based on Diphosphine Ligands"; Chemical Communication, vol. 2002, No. 8, pp. 858-859, (2002).

*Primary Examiner*—Caixia Lu
(74) *Attorney, Agent, or Firm*—Finnegan, Henderson, Farabow, Garrett & Dunner, L.L.P.

(57) ABSTRACT

The invention describes a process for tetramerisation of olefins wherein the product stream of the process contains more than 30% of the tetramer olefin. The process includes the step of contacting an olefinic feedstream with a catalyst system containing a transition metal compound and a heteroatomic ligand.

57 Claims, No Drawings

TETRAMERIZATION OF OLEFINS

CROSS REFERENCE TO RELATED APPLICATIONS

This application is an national phase application based on PCT/ZA2003/000186, filed Dec. 19, 2003, which claims the priority of South African Application No. 2002/10339, filed Dec. 20, 2002, claims the benefit of U.S. Provisional Application No. 60/435,405, filed Dec. 20, 2002, claims the priority of South African Application No. 2003/4632, filed Jun. 13, 2003, claims the benefit of U.S. Provisional Application No. 60/478,379, filed Jun. 13, 2003, claims the priority of South African Application No. 2003/7774, filed Oct. 6, 2003, claims the benefit of U.S. Provisional Application No. 60/509,309, filed Oct. 6, 2003, the content of each of which is incorporated herein by reference in its entirety.

FIELD OF THE INVENTION

This invention relates to the oligomerisation of ethylene. More particularly, the invention relates to a tetramerisation process, a catalyst system for tetramerisation of olefins and the identification and use of ligands for a catalyst system for tetramerisation of olefins.

BACKGROUND OF THE INVENTION

This invention defines a process and catalyst system, that facilitates the production of 1-octene in high selectivity, while avoiding the co-production of significant quantities of butenes, other octene isomers, specific higher oligomers and polyethylene. The catalyst system can also be used for the tetramerisation of other olefins, especially α-olefins.

Despite the well known value of 1-octene, the art does not teach a commercially successful process for the tetramerisation of ethylene to produce 1-octene selectively. Conventional ethylene oligomerisation technologies produce a range of α olefins following either a Schulz-Flory or Poisson product distribution. By definition, these mathematical distributions limit the mass % of the tetramer that can be formed and make a distribution of products. In this regard, it is known from the prior art (U.S. Pat. No. 6,184,428) that a nickel catalyst comprising a chelating ligand, preferably 2-diphenyl phosphino benzoic acid (DPPBA), a nickel compound, preferably $NiCl_2.6H_2O$, and a catalyst activator, preferably sodium tetraphenylborate, catalyse the oligomerisation of ethylene to yield a mixture of linear olefins. The selectivity towards linear C8 α-olefins is claimed to be 19%. Similarly the Shell Higher Olefins Process (SHOP process, U.S. Pat. Nos. 3,676,523 and 3,635,937) using a similar catalyst system is reported to typically yield 11 mass % 1-octene in its product mixture (Chem Systems PERP reports 90-1, 93-6 and 94/95S12).

Ziegler-type technologies based on trialkylaluminium catalysts, independently developed by Gulf Oil Chemicals Company (Chevron, e.g. DE patent 1,443,927) and Ethyl Corporation (BP/Amoco, e.g. U.S. Pat. No. 3,906,053), are also commercially used to oligomerise ethylene to mixtures of olefins that reportedly contain 13-25 mass % 1-octene (Chem Systems PERP reports 90-1, 93-6, and 94/95S12).

The prior art also teaches that chromium-based catalysts containing heteroatomic ligands with both phosphorus and nitrogen heteroatoms selectively catalyse the trimerisation of ethylene to 1-hexene. Examples of such heteroatomic ligands for ethylene trimerisation include bis(2-diethylphosphino-ethyl) amine (WO 03/053891, hereby fully incorporated herein by means of reference) as well as (o-methoxyphenyl)$_2$PN(methyl)P(o-methoxyphenyl)$_2$ (WO 02/04119, hereby fully incorporated herein by means of reference). Both these catalyst systems and processes are very specific for the production of 1-hexene and only yield 1-octene as an impurity (typically less than 3 mass % of the product mixture as disclosed by WO 02/04119). The coordinating phosphorus heteroatoms in (o-methoxyphenyl)$_2$PN(methyl)P(o-methoxyphenyl)$_2$ (WO 02/04119) are spaced apart by one nitrogen atom. It is believed that the nitrogen atom does not coordinate, at least in the absence of an activator, with the chromium and that without any further electron donating atoms on the ligand that it is a bidentate system. Furthermore it is argued that the polar, or electron donating substituents in the ortho-position of the phenyl groups help form a tridentate system, which is generally believed to enhance selectivity towards 1-hexene formation as reiterated by the inventor of WO 02/04119 in Chem. Commun., 2002, 858-859 by stating "This has led us to hypothesise that the potential for ortho-methoxy groups to act as pendent donors and increase the coordinative saturation of the chromium centre is an important factor." To support their hypothesis, the authors of Chem. Commun., 2002, 858-859 showed that the use of (p-methoxyphenyl)$_2$PN(methyl)P(p-methoxyphenyl)$_2$, a compound without any such ortho-polar substituents on at least one of $R^1$, $R^2$, $R^3$ and $R^4$, as a ligand under catalytic conditions resulted in no catalytic activity towards α-olefins. WO 02/04119 (Example 16) teaches the production of octenes using a trimerisation of olefins process and catalyst system. In this instance, 1-butene was co-trimerised with two ethylene molecules to give 25% octenes. However, the nature of these octenes was not disclosed and the applicant believes that they consist of a mixture of linear and branched octenes.

The prior art teaches that high 1-octene selectivities cannot be achieved since expansion of the generally accepted seven-membered metallacycle reaction intermediate for ethylene trimerisation (Chem. Commun., 1989, 674) to a nine-membered metallacycle is unlikely to occur (Organometallics, 2003, 22, 2564; Angew. Chem. Int. Ed., 2003, 42 (7), 808). It is argued that the nine-membered ring is the least favoured medium sized ring and should thus be disfavoured relative to the seven-membered ring (Organometallics, 2003, 22, 2564). In addition, it is also stated by the same authors that, "if a nine-membered ring formed, it would be more likely to grow to an eleven- or thirteen-membered ring . . . . In other words, one would never expect much octene, but formation of some (linear) decene or dodecene would be more reasonable."

Despite the teaching of the opposite, the applicant has now found a process for selectively producing a tetramerised olefin. The applicant has further found that chromium-based catalysts containing mixed heteroatomic ligands with both nitrogen and phosphorus heteroatoms, with polar substituents on the hydrocarbyl or heterohydrocarbyl groups on the phosphorous atoms, can be used to selectively tetramerise ethylene to 1-octene often in excess of 60 mass % selectivity. This high 1-octene selectivity cannot be achieved via conventional one-step ethylene oligomerisation or trimerisation technologies which at most yield 25 mass % 1-octene.

SUMMARY OF THE INVENTION

This invention relates to a process for selectively producing tetrameric products.

This invention specifically relates to a process for selectively producing tetrameric products such as 1-octene from olefins such as ethylene.

The invention relates to a process of selectively producing tetrametric products using a transition metal catalyst system containing a heteroatomic ligand.

According to a first aspect of the invention there is provided a process for tetramerisation of olefins wherein the product of the tetramerisation process is an olefin and makes up more than 30% of the product stream of the process.

According to a second aspect of the invention the tetramerisation process includes the step of contacting an olefinic feedstream with a catalyst system which includes a transition metal and a heteroatomic ligand and wherein the product of the tetramerisation process is an olefin and makes up more than 30% of the product stream of the process.

In this specification, % will be understood to be a mass %.

The term "tetramerisation" generally refers to the reaction of four, and preferably four identical, olefinic monomer units to yield a linear and/or branched olefin.

By heteroatomic is meant a ligand that contains at least two heteroatoms, which can be the same or different, where the heteroatoms may be selected from phosphorus, arsenic, antimony, sulphur, oxygen, bismuth, selenium or nitrogen.

The feedstream will be understood to include an olefin to be tetramerised and can be introduced into the process according to the invention in a continuous or batch fashion.

The product stream will be understood to include a tetramer, which tetramer is produced according to the invention in a continuous or batch fashion.

The feedstream may include an α-olefin and the product stream may include at least 30%, preferably at least 35%, of a tetramerised α-olefin monomer.

The process may include a process for tetramerisation of α-olefins. Under the term α-olefins is meant all hydrocarbon compounds with terminal double bonds. This definition includes ethylene, propylene, 1-butene, isobutylene, 1-pentene, 1-hexene, 1-octene and the like.

The process may include a process for tetramerisation of α-olefins to selectively yield tetrameric α-olefin products.

The olefinic feedstream may include ethylene and the product stream may include at least 30% 1-octene. The process may be a process for tetramerisation of ethylene.

The invention allows the ligand, catalyst system and/or process conditions to be selected to give a product stream of more than 40%, 50%, or 60% α-olefins. It may be preferable, depending on the further use of the product stream, to have such high selectivities of the α-olefin.

The olefinic feedstream may include ethylene and the $(C_6+C_8):(C_4+C_{10})$ ratio in the product stream may be more than 2.5:1.

The olefinic feedstream may include ethylene and the $C_8:C_6$ ratio in the product stream is more than 1.

The ethylene may be contacted with the catalyst system at a pressure of greater than 100 kPa (1 barg) and preferably greater than 1000 kPa (10 barg), more preferably greater than 3000 kPa (30 barg).

The heteroatomic ligand may be described by the following general formula $(R)_nA\text{-}B\text{---}C(R)_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group of which at least one R group is substituted with a polar substituent and n and m is determined by the respective valence and oxidation state of A and C.

A and/or C may be a potential electron donor for coordination with the transition metal.

An electron donor or electron donating substituent is defined as that entity that donates electrons used in chemical, including dative covalent, bond formation.

The heteroatomic ligand may be described by the following general formula $(R^1)(R^2)A\text{-}B\text{---}C(R^3)(R^4)$ where A and C are independently selected from a group which comprises phosphorus, arsenic, antimony, bismuth and nitrogen and B is a linking group between A and C, and $R^1$, $R^2$, $R^3$ and $R^4$ are independently selected from non-aromatic and aromatic, including heteroaromatic, groups of which at least one of $R^1$, $R^2$, $R^3$ and $R^4$ is substituted with a polar substituent.

In some embodiments of the process aspect of the invention, up to four of $R^1$, $R^2$, $R^3$ and $R^4$ may have substituents on the atom adjacent to the atom bound to A or C.

In addition to at least one of $R^1$, $R^2$, $R^3$ and $R^4$ being substituted with a polar substituent, each of $R^1$, $R^2$, $R^3$ and $R^4$ may be aromatic, including heteroaromatic, but preferably not all of $R^1$, $R^2$, $R^3$ and $R^4$, if they all are aromatic, are substituted by any substituent on an atom adjacent to the atom bound to A or C.

In addition to at least one of $R^1$, $R^2$, $R^3$ and $R^4$ being substituted with a polar substituent, not more than two of $R^1$, $R^2$, $R^3$ and $R^4$, if they are aromatic, may have substituents on the atom adjacent to the atom bound to A or C.

Any polar substituents on $R^1$, $R^2$, $R^3$ and $R^4$, if they are aromatic, may preferably not be on the atom adjacent to the atom bound to A or C.

At least one of $R^1$, $R^2$, $R^3$ and $R^4$, if aromatic, may be substituted with a polar substituent on the $2^{nd}$ or further atom from the atom bound to A or C.

Any polar substituent on one or more of $R^1$, $R^2$, $R^3$ and $R^4$ may be electron donating.

Polar is defined by IUPAC as an entity with a permanent electric dipole moment. Polar substituents include methoxy, ethoxy, isopropoxy, $C_3\text{-}C_{20}$ alkoxy, phenoxy, pentafluorophenoxy, trimethylsiloxy, dimethylamino, methylsulfanyl, tosyl, methoxymethyl, methylthiomethyl, 1,3-oxazolyl, methomethoxy, hydroxyl, amino, phosphino, arsino, stibino, sulphate, nitro and the like.

Any of the groups $R^1$, $R^2$, $R^3$ and $R^4$ may independently be linked to one or more of each other or to the linking group B to form a cyclic structure together with A and C, A and B or B and C.

$R^1$, $R^2$, $R^3$ and $R^4$ may be independently selected from a group comprising a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl group.

Preferably, $R^1$, $R^2$, $R^3$ and $R^4$ may independently be selected from a group comprising a phenyl, tolyl, biphenyl, naphthyl, thiophenyl and ethyl group.

A and/or C may be independently oxidised by S, Se, N or O, where the valence of A and/or C allows for such oxidation.

A and C may be independently phosphorus or phosphorus oxidised by S or Se or N or O.

B may be selected from any one of a group comprising: organic linking groups comprising a hydrocarbylene, a substituted hydrocarbylene, a heterohydrocarbylene and a substituted heterohydrocarbylene; inorganic linking groups comprising single atom links; ionic links; and a group comprising methylene, dimethylmethylene, 1,2-ethylene, 1,2-phenylene, 1,2-propylene, 1,2-catecholate, —(CH$_3$)N—N(CH$_3$)—, —B(R$^5$)—, —Si(R$^5$)$_2$—, —P(R$^5$)—, and —N(R$^5$)— where R$^5$ is hydrogen, a hydrocarbyl or substituted hydrocarbyl, a substituted heteroatom or a halogen. Preferably, B may be —N(R$^5$)— and R$^5$ is a hydrocarbyl or a substituted hydrocarbyl group. R$^5$ may be hydrogen or may be selected from the group consisting of alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably R$^5$ may be an isopropyl, a 1-cyclohexylethyl, a 2-methylcyclohexyl or a 2-octyl group.

B may be selected to be a single atom spacer. A single atom linking spacer is defined as a substituted or non-substituted atom that is bound directly to A and C.

The ligand may also contain multiple (R)$_n$A-B—C(R)$_m$ units. Non limiting examples of such ligands include dendrimeric ligands as well as ligands where the individual units are coupled either via one or more of the R groups or via the linking group B. More specific, but non limiting, examples of such ligands may include 1,2-di-(N(P(4-methoxyphenyl)$_2$)$_2$)-benzene, 1,4-di-(N(P(4-methoxyphenyl)$_2$)$_2$)-benzene, N(CH$_2$CH$_2$N(P(4-methoxyphenyl)$_2$)$_2$)$_3$ and 1,4-di-(P(4-methoxyphenyl)N(methyl)P(4-methoxyphenyl)$_2$)-benzene.

The ligands can be prepared using procedures known to one skilled in the art and procedures disclosed in published literature. Examples of ligands are: (3-methoxyphenyl)$_2$PN(methyl)P(3-methoxyphenyl)$_2$, (4-methoxyphenyl)$_2$PN(methyl)P(4-methoxyphenyl)$_2$, (3-methoxyphenyl)$_2$PN(isopropyl)P(3-methoxyphenyl)$_2$, (4-methoxyphenyl)$_2$PN(isopropyl)P(4-methoxyphenyl)$_2$, (4-methoxyphenyl)$_2$PN(2-ethylhexyl)P(4-methoxyphenyl)$_2$, (3-methoxyphenyl)(phenyl)PN(methyl)P(phenyl)$_2$ and (4-methoxyphenyl)(phenyl)PN(methyl)P(phenyl)$_2$, (3-methoxyphenyl)(phenyl)PN(methyl)P(3-methoxyphenyl)(phenyl), (4-methoxyphenyl)(phenyl)PN(methyl)P(4-methoxyphenyl)(phenyl), (3-methoxyphenyl)$_2$PN(methyl)P(phenyl)$_2$ and (4-methoxyphenyl)$_2$PN(methyl)P(phenyl)$_2$, (4-methoxyphenyl)$_2$PN(1-cyclohexylethyl)P(4-methoxyphenyl)$_2$, (4-methoxyphenyl)$_2$PN(2-methylcyclohexyl)P(4-methoxyphenyl)$_2$, (4-methoxyphenyl)$_2$PN(decyl)P(4-methoxyphenyl)$_2$, (4-methoxyphenyl)$_2$PN(pentyl)P(4-methoxyphenyl)$_2$, (4-methoxyphenyl)$_2$PN(benzyl)P(4-methoxyphenyl)$_2$, (4-methoxyphenyl)$_2$PN(phenyl)P(4-methoxyphenyl)$_2$, (4fluorophenyl)$_2$PN(methyl)P(4-fluorophenyl)$_2$, (2-fluorophenyl)$_2$PN(methyl)P(2-fluorophenyl)$_2$, (4-dimethylamino-phenyl)$_2$PN(methyl)P(4-dimethylamino-phenyl)$_2$, (4-methoxyphenyl)$_2$PN(allyl)P(4-methoxyphenyl)$_2$, (phenyl)$_2$PN(isopropyl)P(2-methoxyphenyl)$_2$, (4-(4-(methoxyphenyl)-phenyl)PN(isopropyl)P(4-(4-methoxyphenyl)-phenyl)$_2$ and (4-methoxyphenyl)(phenyl)PN(isopropyl)P(phenyl)$_2$.

The catalyst system may include an activator and the process may include the step of combining in any order a heteroatomic ligand with a transition metal compound and an activator.

The process may include the step of generating a heteroatomic coordination complex in situ from a transition metal compound and a heteroatomic ligand. The process may include the step of adding a pre-formed coordination complex, prepared using a heteroatomic ligand and a transition metal compound, to a reaction mixture, or the step of adding separately to the reactor, a heteroatomic ligand and a transition metal compound such that a heteroatomic coordination complex of a transition metal is generated in situ. By generating a heteroatomic coordination complex in situ is meant that the complex is generated in the medium in which catalysis takes place. Typically, the heteroatomic coordination complex is generated in situ. Typically, the transition metal compound, and heteroatomic ligand are combined (both in situ and ex situ) to provide metal/ligand ratios from about 0.01:100 to 10 000:1, and preferably, from about 0.1:1 to 10:1.

The transition metal may be selected from any one of a group comprising chromium, molybdenum, tungsten, titanium, tantalum, vanadium and zirconium, preferably chromium.

The transition metal compound which, upon mixing with the heteroatomic ligand and an activator, catalyses ethylene tetramerisation in accordance with the invention, may be a simple inorganic or organic salt, a co-ordination or organometallic complex and may be selected from any one of a group comprising chromium trichloride tris-tetrahydrofuran complex, (benzene)tricarbonyl chromium, chromium (III) octanoate, chromium hexacarbonyl, chromium (III) acetylacetonoate and chromium (III) 2-ethylhexanoate. The preferred transition metal compounds include chromium (III) acetylacetonoate and chromium (III) 2-ethylhexanoate.

The heteroatomic ligand can be modified to be attached to a polymer chain so that the resulting heteroatomic coordination complex of the transition metal is soluble at elevated temperatures, but becomes insoluble at 25° C. This approach would enable the recovery of the complex from the reaction mixture for reuse and has been used for other catalyst as described by D. E. Bergbreiter et al., *J. Am. Chem. Soc.*, 1987, 109, 177-179. In a similar vein these transition metal complexes can also be immobilised by binding the heteroatomic ligands for example to silica, silica gel, polysiloxane, alumina backbone or the like as demonstrated, for example, by C. Yuanyin et al., *Chinese J. React. Pol.*, 1992, 1(2), 152-159 for immobilising platinum complexes.

The activator for use in the process may in principle be any compound that generates an active catalyst when combined with the heteroatomic ligand and the transition metal compound. Mixtures of activators may also be used. Suitable compounds include organoaluminium compounds, organoboron compounds, organic salts, such as methyllithium and methylmagnesium bromide, inorganic acids and salts, such as tetrafluoroboric acid etherate, silver tetrafluoroborate, sodium hexafluoroantimonate and the like.

Suitable organoaluminium compounds include compounds of the formula AlR$_3$, where each R is independently a C$_1$-C$_{12}$ alkyl, an oxygen containing moiety or a halide, and compounds such as LiAlH$_4$ and the like. Examples include trimethylaluminium (TMA), triethylaluminium (TEA), triisobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Mixtures of different aluminoxanes may also be used in the process.

Examples of suitable organoboron compounds are boroxines, NaBH$_4$, triethylborane, tris(pentafluorophenyl)borane, tributyl borate and the like.

The activator may also be or contain a compound that acts as a reducing or oxidising agent, such as sodium or zinc metal and the like, or oxygen and the like.

The activator may be selected from alkylaluminoxanes such as methylaluminoxane (MAO) and ethylaluminoxane (EAO) as well as modified alkylaluminoxanes such as modified methylaluminoxane (MMAO). Modified methylaluminoxane (a commercial product from Akzo Nobel) contains modifier groups such as isobutyl or n-octyl groups, in addition to methyl groups.

The transition metal and the aluminoxane may be combined in proportions to provide Al/metal ratios from about 1:1 to 10 000:1, preferably from about 1:1 to 1000:1, and more preferably from 1:1 to 300:1.

The process may include the step of adding to the catalyst system a trialkylaluminium compound in amounts of between 0.01 to 1000 mol per mol of alkylaluminoxane.

It should be noted that aluminoxanes generally also contain considerable quantifies of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

The process may include the step of mixing the components of the catalyst system at any temperature between −20° C. and 250° C. in the presence of an olefin. The applicant has found that the presence of an olefin may stabilise the catalyst system.

The individual components of the catalyst system described herein may be combined simultaneously or sequentially in any order, and in the presence or absence of a solvent, in order to give an active catalyst. The mixing of the catalyst components can be conducted at any temperature between −20° C. and 250° C. The presence of an olefin during the mixing of the catalyst components generally provides a protective effect which may result in improved catalyst performance. The preferred temperature range may be between 20° C. and 100° C.

The catalyst system, in accordance with the invention, or its individual components, may also be immobilised by supporting it on a support material, for example, silica, alumina, $MgCl_2$, zirconia or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components. In some cases, the support material can also act as a component of the activator. This approach would also facilitate the recovery of the catalyst from the reaction mixture for reuse. The concept was, for example, successfully demonstrated with a chromium-based ethylene trimerisation catalyst by T. Monoi and Y. Sasaki, *J. Mol. CatA:Chem.*, 1987, 109, 177-179. In some cases, the support can also act as a catalyst component, for example where such supports contain aluminoxane functionalities or where the support is capable of performing similar chemical functions as an aluminoxane, which is for instance the case with IOLA™ (a commercial product from Grace Davison).

The reaction products or in other words olefin oligomers, as described herein, may be prepared using the disclosed catalyst system by homogeneous liquid phase reaction in the presence or absence of an inert solvent, and/or by slurry reaction where the catalyst system is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The process may therefore also be carried out in an inert solvent. Any inert solvent that does not react with the activator can be used. These inert solvents may include any saturated aliphatic and unsaturated aliphatic and aromatic hydrocarbon and halogenated hydrocarbon. Typical solvents include, but are not limited to, benzene, toluene, xylene, cumene, heptane, methylcyclohexane, methylcyclopentane, cyclohexane, 1-hexene, 1-octene, ionic liquids and the like.

The process may be carried out at pressures from atmospheric to 50000 (500 barg). Ethylene pressures in the range of 1000-7000 kPa (10-70 barg) are preferred. Particularly preferred pressures range from 3000-5000 (30-50 barg).

The process may be carried out at temperatures from −20° C.-250° C. Temperatures in the range of 15-130° C. are preferred. Particularly preferred temperatures range from 35-100° C.

In a preferred embodiment of the invention, the heteroatomic coordination complex and reaction conditions are selected such that the yield of 1-octene from ethylene is greater than 30 mass %, preferably greater than 35 mass %. In this regard yield refers to grams of 1-octene formed per 100 g of total reaction product formed.

In addition to 1-octene, the process may also yield different quantities of 1-butene, 1-hexene, methylcyclopentane, methylene cyclopentane, propylcyclopentane, propylene cyclopentane and specific higher oligomers, depending on the nature of the heteroatomic ligand and the reaction conditions. A number of these products cannot be formed via conventional ethylene oligomerisation and trimerisation technologies in the yields observed in the present invention.

Although the catalyst, its individual components, reagents, solvents and reaction products are generally employed on a once-through basis, any of these materials can, and are indeed preferred to be recycled to some extent in order to minimise production costs.

The process may be carried out in a plant which includes any type of reactor. Examples of such reactors include, but are not limited to, batch reactors, semi-batch reactors and continuous reactors. The plant may include, in combination a) a reactor, b) at least one inlet line into this reactor for olefin reactant and the catalyst system, c) effluent lines from this reactor for oligomerisation reaction products, and d) at least one separator to separate the desired oligomerisation reaction products, wherein the catalyst system may include a heteroatomic coordination complex of a transition metal compound and an activator, as described herein.

In another embodiment of the process the reactor and a separator may be combined to facilitate the simultaneous formation of reaction products and separation of these compounds from the reactor. This process principle is commonly known as reactive distillation. When the catalyst system exhibits no solubility in the solvent or reaction products, and is fixed in the reactor so that it does not exit the reactor with the reactor product, solvent and unreacted olefin, the process principle is commonly known as catalytic distillation.

According to a further aspect of the invention, there is provided a catalyst system, as described above, for the tetramerisation of olefins. The catalyst system may include a heteroatomic ligand as described above and a transition metal. The catalyst system may also include an activator as described above.

The heteroatomic ligand may be described by the following general formula $(R)_nA-B-C(R)_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group of which at least one R group is substituted with a polar substituent and n and m is determined by the respective valence and oxidation state of A and C.

A and/or C may be a potential electron donor for coordination with the transition metal.

An electron donor or electron donating substituent is defined as that entity that donates electrons used in chemical, including dative covalent, bond formation.

The heteroatomic ligand may be described by the following general formula $(R^1)(R^2)A-B-C(R^3)(R^4)$ where A and C are independently selected from a group which comprises phosphorus, arsenic, antimony, bismuth and nitrogen and B is a linking group between A and C, and $R^1$, $R^2$, $R^3$ and $R^4$ are independently selected from non-aromatic and aromatic, including heteroaromatic, groups of which at least one of $R^1$, $R^2$, $R^3$ and $R^4$ is substituted with a polar substituent.

In addition to at least one of $R^1$, $R^2$, $R^3$ and $R^4$ being substituted with a polar substituent, each of $R^1$, $R^2$, $R^3$ and $R^4$ may be aromatic, including heteroaromatic, but preferably not all of $R^1$, $R^2$, $R^3$ and $R^4$, if they all are aromatic, are substituted by any substituent on an atom adjacent to the atom bound to A or C.

In addition to at least one of $R^1$, $R^2$, $R^3$ and $R^4$ being substituted with a polar substituent, not more than two of $R^1$, $R^2$, $R^3$ and $R^4$, if they are aromatic, may have substituents on the atom adjacent to the atom bound to A or C.

Any polar substituents on $R^1$, $R^2$, $R^3$ and $R^4$, if they are aromatic, may preferably not be on the atom adjacent to the atom bound to A or C.

Any polar substituent on one or more of $R^1$, $R^2$, $R^3$ and $R^4$ may be electron donating.

Polar is defined as an entity with a permanent electric dipole moment Polar substituents include methoxy, ethoxy, isopropoxy, $C_3$-$C_{20}$ alkoxy, phenoxy, pentafluorophenoxy, trimethylsiloxy, dimethylamino, methylsulfanyl, tosyl, methoxymethyl, methylthiomethyl, 1,3-oxazolyl, methomethoxy, hydroxyl, amino, phosphino, arsino, stibino, sulphate, nitro and the like.

Any of the groups $R^1$, $R^2$, $R^3$ and $R^4$ may independently be linked to one or more of each other or to the linking group B to form a cyclic structure together with A and C, A and B or B and C.

$R^1$, $R^2$, $R^3$ and $R^4$ may be independently selected from a group comprising a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl group. Preferably, $R^1$, $R^2$, $R^3$ and $R^4$ may independently be selected from a group comprising a phenyl, tolyl, biphenyl, naphthyl, thiophenyl and ethyl group.

A and/or C may be independently oxidised by S, Se, N or O, where the valence of A and/or C allows for such oxidation.

A and C may be independently phosphorus or phosphorus oxidised by S or Se or N or O.

B may be selected from any one of a group comprising: organic linking groups comprising a hydrocarbyl, substituted hydrocarbyl, heterohydrocarbyl and a substituted heterohydrocarbyl; inorganic linking groups comprising single atom links; ionic links; and a group comprising methylene, dimethylmethylene, 1,2-ethane, 1,2-phenylene, 1,2-propane, 1,2-catechol, 1,2-dimethylhydrazine, —B($R^5$)—, —Si($R^5$)$_2$—, —P($R^5$)— and —N($R^5$)— where $R^5$ is hydrogen, a hydrocarbyl or substituted hydrocarbyl, a substituted heteroatom or a halogen. Preferably, B may be —N($R^5$)— and $R^5$ is a hydrocarbyl or a substituted hydrocarbyl group. $R^5$ may be hydrogen or may be selected from the groups consisting of alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably $R^5$ may be an isopropyl, a 1-cyclohexylethyl, a 2-methylcyclohexyl or a 2-octyl group.

B may be selected to be a single atom spacer. A single atom linking spacer is defined as a substituted or non-substituted atom that is bound directly to A and C.

The ligand may also contain multiple $(R)_nA-B-C(R)_m$ units. Not limiting examples of such ligands include dendrimeric ligands as well as ligands where the individual units are coupled either via one or more of the R groups or via the linking group B. More specific, but not limiting, examples of such ligands may include 1,2-di-(N(P(4-phenyl)$_2$)$_2$)-benzene, 1,4di-(N(P(4methoxyphenyl)$_2$)$_2$)-benzene, N(CH$_2$CH$_2$N(P(4-methoxyphenyl)$_2$)$_2$)$_3$ and 1,4-di-(P(4methoxyphenyl)N(methyl)P(4-methoxyphenyl)$_2$)-benzene.

The ligands can be prepared using procedures known to one skilled in the art and procedures disclosed in published literature. Examples of ligands are: (3-methoxyphenyl)$_2$PN(methyl)P(3-methoxyphenyl)$_2$, (4-methoxyphenyl)$_2$PN(methyl)P(4-methoxyphenyl)$_2$, (3-methoxyphenyl)$_2$PN(isopropyl)P(3-methoxyphenyl)$_2$, (4-methoxyphenyl)$_2$PN(isopropyl)P(4-methoxyphenyl)$_2$, (4-methoxyphenyl)$_2$PN(2-ethylhexyl)P(4methoxyphenyl)$_2$, (3-methoxyphenyl)(phenyl)PN(methyl)P(phenyl)$_2$, and (4-methoxyphenyl)(phenyl)PN(methyl)P(phenyl)$_2$, (3-methoxyphenyl)(phenyl)PN(methyl)P(3-methoxyphenyl)(phenyl), (4-methoxyphenyl)(phenyl)PN(methyl)P(4-methoxyphenyl)(phenyl), (3-methoxyphenyl)$_2$PN(methyl)P(phenyl)$_2$ and (4-methoxyphenyl)$_2$PN(methyl)P(phenyl)$_2$, (4-methoxyphenyl)$_2$PN(1-cyclohexylethyl)P(4-methoxyphenyl)$_2$, (4-methoxyphenyl)$_2$PN(2-methylcyclohexyl)P(4-methoxyphenyl)$_2$, (4-methoxyphenyl)$_2$PN(decyl)P(4-methoxyphenyl)$_2$, (4-methoxyphenyl)$_2$PN(pentyl)P(4-methoxyphenyl)$_2$, (4-methoxyphenyl)$_2$PN(benzyl)P(4-methoxyphenyl)$_2$, (4-methoxyphenyl)$_2$PN(phenyl)P(4-methoxyphenyl)$_2$, (4fluorophenyl)$_2$PN(methyl)P(4-fluorophenyl)$_2$, (2-fluorophenyl)$_2$PN(methyl)P(2-fluorophenyl)$_2$, (4dimethylamino-phenyl)$_2$PN(methyl)P(4-dimethylamino-phenyl)$_2$, (4methoxyphenyl)$_2$PN(allyl)P(4methoxyphenyl)$_2$, (phenyl)$_2$PN(isopropyl)P(2-methoxyphenyl)$_2$, (4-(4-methoxyphenyl)-phenyl)$_2$PN(isopropyl)P(4-(4-methoxyphenyl)-phenyl)$_2$ and (4-methoxyphenyl)(phenyl)PN(isopropyl)P(phenyl)$_2$.

The transition metal may be selected from any one of a group comprising chromium, molybdenum, tungsten, titanium, tantalum, vanadium and zirconium, preferably chromium.

The transition metal may be derived from a transition metal compound selected from a simple inorganic or organic salt, a co-ordination or organometallic complex, which may be selected from a group comprising chromium trichloride tris-tetrahydrofuran complex, (benzene)tricarbonyl chromium, chromium (III) octanoate, chromium (III) acetylacetonoate, chromium hexacarbonyl, and chromium (III)

2-ethylhexanoate. The preferred transition metal compounds include chromium (III) acetylacetonate and chromium (III) 2-ethylhexanoate.

The transition metal compound and heteroatomic ligand may have metal/ligand ratios from about 0.01:100 to 10 000:1, preferably from about 0.1:1 to 10:1.

The catalyst system may also include an activator as described above.

The activator may in principle be any compound that generates an active catalyst when combined with the heteroatomic ligand and the transition metal compound. Mixtures of activators may also be used. Suitable compounds include organoaluminium compounds, organoboron compounds, organic salts, such as methyllithium and methylmagnesium bromide, inorganic acids and salts, such as tetrafluoroboric acid etherate, silver tetrafluoroborate, sodium hexafluoroantimonate and the like.

The activator may be selected from alkylaluminoxanes such as methylaluminoxane (MAO) and ethylaluminoxane (EAO) as well as modified alkylaluminoxanes such as modified methylaluminoxane (MMAO). Modified methylaluminoxane (a commercial product from Akzo Nobel) contains modifier groups such as isobutyl or n-octyl groups, in addition to methyl groups. The transition metal and the aluminoxane may be in such proportions relative to each other to provide Al/metal ratios from about 1:1 to 10 000:1, preferably from about 1:1 to 1000:1, and more preferably from 1:1 to 300:1.

The catalyst system may also include a trialkylaluminium compound in amounts of between 0.01 to 100 mol per mol of aluminoxane.

According to an even further aspect of the invention, there is provided a ligand, as described above, for a catalyst system, as described above, for the tetramerisation of olefins.

The invention also extends to the identification and use of ligands suitable for use in a tetramerisation of olefins process or catalyst system.

EXAMPLES OF PERFORMING THE INVENTION

The invention will now be described with reference to the following examples which are not in any way intended to limit the scope of the invention. The individual components of the examples may conceivably be, omitted or substituted and, although not necessarily ideal, the invention may conceivably still be performed and these components are not to be taken as essential to the working of the invention.

In the examples that follow all procedures were carried out under inert conditions, using pre-dried reagents. Chemicals were obtained from Sigma-Aldrich or Strem Chemicals unless stated otherwise. All trialkylaluminium and aluminoxane compounds and solutions thereof were obtained from Crompton Gmbh, Akzo Nobel and Albemarle Corporation. In all the examples, the molar mass of methylaluminoxane (MAO) was taken to be 58.016 g/mol, corresponding to the ($CH_3$—Al—O) unit, in order to calculate the molar quantities of MAO used in the preparation of the catalysts described in the examples-below. Similarly the molar mass of ethylaluminoxane (EAO) was taken as 72.042 g/mol, corresponding to the ($CH_3CH_2$—Al—O) building block, and that of modified methylaluminoxane prepared from a 70:30 mixture of trimethylaluminium and tri-isobutylaluminium as 70.7 g/mol corresponding to the ($Me_{0.70}isonBu_{0.30}$—Al—O) unit. Ethylene oligomerisation products were analysed by GC-MS and GC-FID.

The mixed heteroatomic PNP ligands were made by reacting amines and phosphine chlorides $R_2PCl$ as described in (a) Ewart et al, *J. Chem. Soc.* 1964, 1543; (b) Dossett, S. J. et al., *Chem. Commun.*, 2001, 8, 699; (c) Balakrishna, M. S. et al, *J. Organomet. Chem.* 1990, 390, 2, 203). The respective phosphine chlorides $R_2PCl$ were prepared as described in literature (Casalnuovo, A. L. et al, *J. Am. Chem. Soc.* 1994, 116, 22, 9869; Rajanbabu, T. V. et al, *J. Org. Chem.* 1997, 62, 17, 6012).

Example 1

Preparation of the (4-methoxyphenyl)$_2$PN(isopropyl)P(4-phenyl)$_2$ ligand

Example 1a

Preparation of N,N-Diisopropylphosphoramide dichloride

Diisopropylamine (70 ml, 0.50 mol) in toluene (80 ml) was added to a solution of $PCl_3$ (21.87 ml, 0.25 mol) in toluene (80 ml) at −10° C. The mixture was stirred for two hours and then allowed to warm to room temperature. The solution was stirred for a further hour after which it was filtered through a pad of celite. The product (35 g, 0.17 mol, 68%) was obtained after removal of the solvent. $^{31}P\{H\}$ NMR: 170 ppm

Example 1b

Preparation of 4-methoxyphenyl-magnesium bromide

Magnesium turnings (9.11 g, 0.375 mol) were treated with 4-bromoanisole (9.39 ml, 75 mmol) in THF (100 ml). A vigorous reaction ensued which was cooled in an ice bath. Once the reaction had dissipated, the reaction mixture was heated under reflux for 2 hours yielding the Grignard reagent.

Example 1c

Preparation of Bis(4-methoxyphenyl)phosphorus chloride

The Grignard reagent was added to N,N-diisopropylphosphoramide dichloride (6.64 ml, 36 mmol) in THF (100 ml) at 0° C. After stirring at room temperature overnight the mixture was diluted with cyclohexane (200 ml) and dry HCl gas was bubbled through the solution for 0.5 hours. After filtration of the precipitate, the solvent was removed to give a mixture of the phosphine chloride and bromide in an 80% yield. This crude product was not isolated and all was used in the next step.

Example 1d

Preparation of (4-methoxyphenyl)$_2$PN(isopropyl)P(4-methoxyphenyl)$_2$

To a solution of the crude Bis(4-methoxyphenyl) phosphorus chloride (28.8 mmol calculated from crude reaction mixture) in DCM (80 ml) and triethylamine (15 ml) at 0° C. was added isopropylamine (1.11 ml, 13 mmol). The reaction was stirred for 30 min after which the ice bath was removed. After stirring for a total of 14 hrs the solution was filtered to remove the triethylammonium salt formed. The product was isolated after crystallisation in a 77% yield. $^{31}P\{H\}$ NMR: 47.4 ppm (broad singlet)

Example 2

Ethylene tetramerisation reaction using Cr (III) acetylacetonoate, (4-methoxyphenyl)$_2$PN(methyl)P(4-methoxyphenyl)$_2$ and MAO A solution of 30.0 mg of (4-methoxyphenyl)$_2$PN(methyl)P(4-methoxyphenyl)$_2$ (0.066 mmol) in 10 ml of toluene was added to a solution of 11.5 mg chromium (III) acetylacetonoate (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was maintained at 65° C., while the ethylene pressure was kept at 3000 kPa (30 barg). Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 0.2254 g of polyethylene. The GC analyses indicated that the reaction mixture contained 38.50 g oligomers. The product distribution of this example is summarised in Table 1.

Example 3

Ethylene tetramerisation reaction using Cr (III) acetylacetonoate, (3-methoxyphenyl)$_2$PN(methyl)P(3-methoxyphenyl)$_2$ and MAO A solution of 30.0 mg of (3-methoxyphenyl)$_2$PN(methyl)P(3-methoxyphenyl)$_2$ (0.066 mmol) in 10 ml of toluene was added to a solution of 11.5 mg chromium (III) acetylacetonoate (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was maintained at 65° C., while the ethylene pressure was kept at 3000 kPa (30 barg). Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.2269 g of polyethylene. The GC analyses indicated that the reaction mixture contained 9.71 g oligomers. The product distribution of this example is summarised in Table 1.

Example 4

Ethylene tetramerisation reaction using Cr (III) acetylacetonoate, (4-methoxyphenyl)$_2$PN(isopropyl)P(4-methoxyphenyl)$_2$ and MAO A solution of 36.1 mg of (4-methoxyphenyl)$_2$PN(isopropyl)P(4-methoxyphenyl)$_2$ (0.066 mmol) in 10 ml of toluene was added to a solution of 11.5 mg chromium (III) acetylacetonoate (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was maintained at 65° C., while the ethylene pressure was kept at 3000 kPa (30 barg). Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 0.7105 g of polyethylene. The GC analyses indicated that the reaction mixture contained 61.33 g oligomers. The product distribution of this example is summarised in Table 1.

Example 5

Ethylene tetramerisation reaction using Cr (III) acetylacetonoate, (4-methoxyphenyl)$_2$PN(isopropyl)P(4-methoxyphenyl)$_2$ and MAO A solution of 36.1 mg of (4-methoxyphenyl)$_2$PN(isopropyl)P(4-methoxyphenyl)$_2$ (0.066 mmol) in 10 ml of toluene was added to a solution of 11.5 mg chromium (III) acetylacetonoate (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 12 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 2.3010 g of polyethylene. The GC analyses indicated that the reaction mixture contained 73.53 g oligomers. The product distribution of this example is summarised in Table 1.

Example 6

Ethylene tetramerisation reaction using Cr (III) acetylacetonoate, (4-methoxyphenyl)$_2$PN(isopropyl)P(4-methoxyphenyl)$_2$ and MAO A solution of 16.4 mg of (4-methoxyphenyl)$_2$PN(isopropyl)P(4-methoxyphenyl)$_2$ (0.03 mmol) in 10 ml of cyclohexane was added to a solution of 5.2 mg chromium (III) acetylacetonate (0.015 mmol) in 10 ml cyclohexane in a Schlenk vessel. The mixture was stirred for 5 min at ambient temperature and was then transferred to a 300 ml pressure reactor (autoclave) containing a mixture of cyclohexane (80 ml) and MAO (methylaluminoxane in toluene, 4.5 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 11 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.9168 g of polyethylene. The GC analyses indicated that the reaction mixture contained 62.72 g oligomers. The product distribution of this example is summarised in Table 1.

Example 7

Ethylene tetramerisation reaction using Cr (III) acetylacetonoate, (4-methoxyphenyl)$_2$PN(isopropyl)P(4-methoxyphenyl)$_2$ and MAO A solution of 9.8 mg of (4-methoxyphenyl)$_2$PN(isopropyl)P(4-methoxyphenyl)$_2$ (0.018 mmol) in 10 ml of toluene was added to a solution of 5.2 mg chromium (III) acetylacetonate (0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.5 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 21 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 0.8280 g of polyethylene. The GC analyses indicated that the reaction mixture contained 69.17 g oligomers. The product distribution of this example is summarised in Table 1.

Example 8

Ethylene tetramerisation reaction using CrCl$_3$.THF$_3$, (4-methoxyphenyl)$_2$PN(isopropyl)P(4-methoxyphenyl)$_2$ and MAO A solution of 9.8 mg of (4-methoxyphenyl)$_2$PN(isopropyl)P(4-methoxyphenyl)$_2$ (0.018 mmol) in 10 ml of toluene was added to a solution of 5.6 mg CrCl$_3$.THF$_3$ (0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.5 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.0831 g of polyethylene. The GC analyses indicated that the reaction mixture contained 42.72 g oligomers. The product distribution of this example is summarised in Table 1.

Example 9

Ethylene tetramerisation reaction using Cr (III) 2-ethylhexanoate, (4-methoxyphenyl)$_2$PN(isopropyl)P(4-methoxyphenyl)$_2$ and MAO A solution of 9.8 mg of (4-methoxyphenyl)$_2$PN(isopropyl)P(4-methoxyphenyl)$_2$ (0.018 mmol) in 10 ml of toluene was added to a solution of 10.2 mg Cr (III) 2-ethylhexanoate (70% in mineral oil, 0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.5 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.52 g of polyethylene. The GC analyses indicated that the reaction mixture contained 61.27 g oligomers. The product distribution of this example is summarised in Table 1.

Example 10

Ethylene tetramerisation reaction using Cr (III) octanoanoate, (4-methoxyphenyl)$_2$PN(isopropyl)P(4-methoxyphenyl)$_2$ and MAO A solution of 9.8 mg of (4-methoxyphenyl)$_2$PN(isopropyl) P(4-methoxyphenyl)$_2$ (0.018 mmol) in 10 ml of toluene was added to a solution of 10.3 mg Cr (III) octanoate (70% in toluene, 0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.5 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 40 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 0.3773 g of polyethylene. The GC analyses indicated that the reaction mixture contained 18.91 g oligomers. The product distribution of this example is summarised in Table 1.

Example 11

Ethylene tetramerisation reaction using Cr (III) acetylacetonoate, (4-methoxyphenyl)$_2$PN(isopropyl) P(4-methoxyphenyl)$_2$ and MAO A solution of 6.6 mg of (4-methoxyphenyl)$_2$PN(isopropyl) P(4-methoxyphenyl)$_2$ (0.012 mmol) in 10 ml of toluene was added to a solution of 3.5 mg chromium (III) acetylacetonoate (0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 3.0 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 30 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.3958 g of polyethylene. The GC analyses indicated that the reaction mixture contained 54.52 g oligomers. The product distribution of this example is summarised in Table 1.

Example 12

Ethylene tetramerisation reaction using Cr (III) acetylacetonoate, (4-methoxyphenyl)$_2$PN(isopropyl) P(4-methoxyphenyl)$_2$ and MAO A solution of 9.8 mg of (4-methoxyphenyl)$_2$PN(isopropyl) P(4-methoxyphenyl)$_2$ (0.018 mmol) in 10 ml of toluene was added to a solution of 5.2 mg chromium (III) acetylacetonoate (0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane in toluene, 2.25 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 15 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 0.5010 g of polyethylene. The GC analyses indicated that the reaction mixture contained 70.87 g oligomers. The product distribution of this example is summarised in Table 1.

Example 13

Ethylene tetramerisation reaction using Cr (III) acetylacetonoate, (4-methoxyphenyl)$_2$PN(isopropyl) P(4-methoxyphenyl)$_2$ and MMAO-3A A solution of 16.4 mg of (4-methoxyphenyl)$_2$PN(isopropyl)P(4-methoxyphenyl)$_2$ (0.03 mmol) in 10 ml of toluene was added to a solution of 5.2 mg chromium (III) acetylacetonoate (0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MMAO-3A (modified methylaluminoxane in heptanes, 4.5 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 22 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.76 g of polyethylene. The GC analyses indicated that the reaction mixture contained 50.42 g oligomers. The product distribution of this example is summarised in Table 1.

Example 14

Ethylene tetramerisation reaction using Cr (III) acetylacetonoate, (4-methoxyphenyl)$_2$PN(isopropyl)P(4-methoxyphenyl)$_2$ and EAO/TMA A solution of 36.1 mg of (4-methoxyphenyl)$_2$PN(isopropyl)P(4-methoxyphenyl)$_2$ (0.066 mmol) in 10 ml of toluene was added to a solution of 5.2 mg chromium (III) acetylacetonoate (0.015 mmol) in 10 ml toluene in a Schlenk vessel. The mixture was stirred for 5 min at ambient temperature and was then transferred to a 300 ml pressure reactor (autoclave) containing a mixture of toluene (80 ml), EAO (ethylaluminoxane in toluene, 33 mmol) and TMA (trimethylaluminium, 8.25 mmol) at 40° C. The pressure reactor was charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 60 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 0.189 g of polyethylene. The GC analyses indicated that the reaction mixture contained 40.97 g oligomers. The product distribution of this example is summarised in Table 1.

Example 15

Ethylene tetramerisation reaction using Cr (III) acetylacetonoate, (4-methoxyphenyl)$_2$PN(isopropyl)P(4-methoxyphenyl)$_2$ and MAO in the presence of H$_2$ A solution of 16.4 mg of (4-methoxyphenyl)$_2$PN(isopropyl)P(4-methoxyphenyl)$_2$ (0.03 mmol) in 10 ml of toluene was added to a solution of 5.2 mg chromium (III) acetylacetonoate (0.015 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane in toluene, 4.5 mmol) at 40° C. The pressure reactor was first charged with hydrogen to a pressure of approximately 250 kPa (2.5 barg) and subsequently with ethylene to 4500 kPa (45 barg) after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 15 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 1.2060 g of polyethylene. The GC analyses indicated that the reaction mixture contained 81.51 g oligomers. The product distribution of this example is summarised in Table 1.

Example 16

Ethylene tetramerisation reaction using Cr (III) acetylacetonoate, (phenyl)$_2$PN(isopropyl)P(2-methoxyphenyl)$_2$ and MAO A solution of 32.2 mg of (phenyl)$_2$PN(isopropyl)P(2-methoxyphenyl)$_2$ (0.066 mmol) in 10 ml of toluene was added to a solution of 11.5 mg chromium (III) acetylacetonoate (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane in toluene, 4.5 mmol) at 40° C. The pressure reactor was first charged with ethylene after which the reactor temperature was maintained at 45° C., while the ethylene pressure was kept at 4500 kPa (45 barg). Thorough mixing was ensured throughout by mixing speeds of 1100 RPM's using a gas entraining stirrer. The reaction was terminated after 15 minutes by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid wax/polymeric products. These solid products were dried overnight in an oven at 100° C. and then weighed to yield 6.82 g of polyethylene. The GC analyses indicated that the reaction mixture contained 38.33 g oligomers. The product distribution of this example is summarised in Table 1.

TABLE 1

Ethylene tetramerisation runs: Examples 2–16

| Example | Activity g prod./g Cr | Total Product g | Solids Wt % | Liquids Wt % | Liquid Product Distribution Wt % | | | | | 1-Octene in $C_8$ Wt % |
|---|---|---|---|---|---|---|---|---|---|---|
| | | | | | $C_4$ | $C_6$ | $C_8$ | $C_{10}$ | $C_{11+}$ | |
| 2 | 22622 | 38.72 | 0.58 | 99.42 | 3.2 | 26.0 | 50.1 | 4.2 | 16.0 | 93.5 |
| 3 | 6376 | 10.94 | 11.21 | 88.79 | 2.8 | 33.8 | 37.5 | 1.4 | 19.5 | 92.2 |
| 4 | 36156 | 62.04 | 1.15 | 98.08 | 0.5 | 39.1 | 51.5 | 2.9 | 5.8 | 98.8 |
| 5 | 44301 | 75.83 | 3.03 | 96.97 | 1.2 | 24.4 | 61.1 | 1.0 | 10.7 | 98.0 |
| 6 | 83515 | 62.64 | 2.97 | 97.03 | 1.0 | 24.5 | 54.9 | 1.0 | 16.0 | 97.0 |
| 7 | 90432 | 69.99 | 1.18 | 98.82 | 1.1 | 23.2 | 62.9 | 0.6 | 10.9 | 98.4 |
| 8 | 56365 | 43.80 | 2.47 | 97.53 | 1.1 | 24.4 | 69.3 | 0.8 | 3.6 | 98.9 |
| 9 | 80510 | 62.79 | 2.42 | 97.58 | 1.3 | 23.1 | 62.7 | 2.6 | 10.1 | 98.0 |
| 10 | 24924 | 19.29 | 1.96 | 98.04 | 1.0 | 23.4 | 67.3 | 0.9 | 6.4 | 98.6 |
| 11 | 107331 | 55.92 | 2.50 | 97.50 | 1.3 | 25.4 | 63.0 | 1.0 | 7.8 | 98.0 |
| 12 | 92214 | 71.37 | 0.70 | 99.30 | 1.0 | 23.5 | 65.4 | 0.9 | 3.1 | 98.6 |
| 13 | 66911 | 52.18 | 3.37 | 96.86 | 2.0 | 18.3 | 65.8 | 2.7 | 11.1 | 98.4 |
| 14 | 23987 | 41.16 | 0.46 | 99.54 | 2.1 | 28.3 | 63.5 | 1.4 | 4.5 | 98.2 |
| 15 | 106055 | 82.71 | 1.46 | 98.54 | 1.9 | 32.6 | 63.2 | 1.1 | 1.1 | 98.0 |
| 16 | 26310 | 45.15 | 15.11 | 84.89 | 0.3 | 36.7 | 46.3 | 5.8 | 10.6 | 98.5 |

The invention claimed is:

1. A process for the oligomerisation of olefins comprising contacting an olefinic feedstream with a catalyst system which includes the combination of:
   a transition metal compound; and
   a heteroatomic ligand described by the following general formula $(R)_n A\text{-}B\text{---}C(R)_m$ where
   A and C are independently an atom selected from the group consisting of phosphorus, arsenic, antimony, oxygen, bismuth, sulphur, selenium and nitrogen or said atom oxidized by S, Se, N or O, where the valance of A and/or C allows for such oxidation;
   B is a linking group between A and C;
   the R groups are the same or different and each R is independently selected from a homo hydrocarbyl group and a heterohydrocarbyl group, and at least one R has a polar substituent; and
   n and m for each R is independently determined by the respective valence and oxidation state of A and C; and
   provided that when the heteroatomic ligand is described by the following general formula $(R^1)(R^2)A\text{-}B\text{---}C(R^3)(R^4)$ wherein
   A and C are independently selected from the group consisting of phosphorus, arsenic, antimony, bismuth and nitrogen;
   B is a linking group between A and C; and
   each of $R^1$, $R^2$, $R^3$ and $R^4$ is independently selected from the group consisting of a non-aromatic group, an aromatic group, and a heteroaromatic group;
   at least one of $R^1$, $R^2$, $R^3$ and $R^4$, if aromatic, has a polar substituent on a $2^{nd}$ or further atom from the atom bound to A or C and provided that any polar substituents that $R^1$, $R^2$, $R^3$ and $R^4$ may have, if they are aromatic, are not on the atom adjacent to the atom bound to A or C.

2. The process as claimed in claim 1, wherein the heteroatomic ligand is described by the following general formula $(R^1)(R^2)A\text{-}B\text{---}C(R^3)(R^4)$ where A and C are independently selected from the group consisting of phosphorus, arsenic, antimony, bismuth, and nitrogen; B is a linking group between A and C; and each of $R^1$, $R^2$, $R^3$ and $R^4$ is independently selected from the group consisting of a non-aromatic group, an aromatic group, and a heteroaromatic group.

3. The process as claimed in claim 2, wherein up to four of $R^1$, $R^2$, $R^3$ and $R^4$ have substituents on the atom adjacent to the atom bound to A or C.

4. The process as claimed in claim 2, which is a tetramerisation process and wherein each of $R^1$, $R^2$, $R^3$ and $R^4$ is aromatic, including heteroaromatic, but not all of $R^1$, $R^2$, $R^3$ and $R^4$ have a substituent on an atom adjacent to the atom bound to A or C.

5. The process as claimed in claim 4, wherein not more than two of $R^1$, $R^2$, $R^3$ and $R^4$ have substituents on the atom adjacent to the atom bound to A or C.

6. The process as claimed in claim 2, wherein each polar substituent that one or more of $R^1$, $R^2$, $R^3$ and $R^4$ may have is electron donating.

7. The process as claimed in claim 4, wherein the feedstream includes an α-olefin and the product stream includes at least 30% of a tetramerised α-olefin monomer.

8. The process as claimed in claim 7, wherein the olefinic feedstream includes ethylene and the product stream includes at least 30% 1-octene.

9. The process as claimed in claim 1, wherein the olefinic feedstream includes ethylene and wherein the $(C_6+C_8):(C_4+C_{10})$ ratio in the product stream is more than 2.5:1.

10. The process as claimed in claim 1, wherein the olefinic feedstream includes ethylene and wherein the C8:C6 ratio in the product stream is more than 1.

11. The process as claimed in claim 1, wherein the pressure is greater than 100 kPa (1 barg).

12. The process as claimed in claim 8, wherein ethylene is contacted with the catalyst system at a pressure of more than 1000 kPa (10 barg).

13. The process as claimed in claim 1, wherein A and/or C are a potential electron donor for coordination with the transition metal.

14. The process as claimed in claim 1, wherein B is selected from the group consisting of an organic linking group comprising a hydrocarbylene, a substituted hydrocarbylene, a hetero hydrocarbylene or a substituted hetero hydrocarbylene; an inorganic linking group comprising a single atom linking spacer; and a group comprising methylene, dimethylmethylene, 1,2-ethylene, 1,2-phenylene, 1,2-propylene, 1,2-catecholate, —(CH$_3$)N—N(CH$_3$)—, —B(R$^5$)—, —Si(R$^5$)$_2$—, —P(R$^5$)— or —N(R$^5$)—, where R$^5$ is hydrogen, a hydrocarbyl or substituted hydrocarbyl, a substituted heteroatom or a halogen.

15. The process as claimed in claim 14, wherein B is a single atom linking spacer.

16. The process as claimed in claim 14, wherein B is —N(R$^5$)—, wherein R$^5$ is selected from the groups consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents.

17. The process as claimed in claim 1, wherein A and/or C is independently oxidised by S, Se, N or O, where the valence of A and/or C allows for such oxidation.

18. The process as claimed in claim 1, wherein A and C is independently phosphorous or phosphorous oxidised by S or Se or N or O.

19. The process as claimed in claim 2, wherein R$^1$, R$^2$, R$^3$ and R$^4$ are independently selected from the group consisting of benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl group.

20. The process as claimed in claim 1, wherein the ligand is selected from the group consisting of (3-methoxyphenyl)$_2$PN(methyl)P(3-methoxyphenyl)$_2$, (4-methoxyphenyl)$_2$PN(methyl)P(4-methoxyphenyl)$_2$(3-methoxyphenyl)$_2$PN(isopropyl)P(3-methoxyphenyl)$_2$, (4-methoxyphenyl)$_2$PN(isopropyl)P(4-methoxyphenyl)$_2$, (4-methoxyphenyl)$_2$PN(2-ethylhexyl)P(4-methoxyphenyl)$_2$, (3-methoxyphenyl)(phenyl)PN(methyl)P(phenyl)$_2$, (4-methoxyphenyl)(phenyl)PN(methyl)P(phenyl)$_2$, (3-methoxyphenyl)(phenyl)PN(methyl)P(3-methoxyphenyl)(phenyl), (4-methoxyphenyl)(phenyl)PN(methyl)P(4-methoxyphenyl)(phenyl), (3-methoxyphenyl)$_2$PN(methyl)P(phenyl)$_2$, (4-methoxyphenyl)$_2$PN(methyl)P(phenyl)$_2$, (4-methoxyphenyl)$_2$PN(1-cyclohexylethyl)P(4-methoxyphenyl)$_2$, (4-methoxyphenyl)$_2$PN(2-methylcyclohexyl)P(4-methoxyphenyl)$_2$, (4-methoxyphenyl)$_2$PN(decyl)P(4-methoxyphenyl)$_2$, (4-methoxyphenyl)$_2$PN(pentyl)P(4-methoxyphenyl)$_2$, (4-methoxyphenyl)$_2$PN(benzyl)P(4-methoxyphenyl)$_2$, (4-methoxyphenyl)$_2$PN(phenyl)P(4-methoxyphenyl)$_2$, (4-fluorophenyl)$_2$PN(methyl)P(4-fluorophenyl)$_2$, 3-fluorophenyl)$_2$PN(methyl)P(3-fluorophenyl)$_2$, (4-dimethylamino-phenyl)$_2$PN(methyl)P(4-dimethylamino-phenyl)$_2$, (4-methoxyphenyl)$_2$PN(allyl)P(4-methoxyphenyl)$_2$, (4-(4-methoxyphenyl)-phenyl)$_2$PN(isopropyl)P(4-(4-methoxyphenyl)-phenyl)$_2$ and (4-methoxyphenyl)(phenyl)PN(isopropyl)P(phenyl)$_2$.

21. The process as claimed in claim 1, wherein the catalyst system is prepared by combining in any order the heteroatomic ligand with the transition metal compound and an activator.

22. The process as claimed in claim 21, which includes the step of adding a pre-formed coordination complex, prepared using the heteroatomic ligand and the transition metal compound, to a reaction mixture containing the activator.

23. The process as claimed in claim 21, which includes the step of generating a heteroatomic coordination complex in situ from the transition metal compound and a heteroatomic ligand.

24. The process as claimed in claim 1, wherein the transition metal in the transition metal compound is selected from the group consisting of chromium, molybdenum, tungsten, titanium, tantalum, vanadium and zirconium.

25. The process as claimed in claim 24, wherein the transition metal is chromium.

26. The process as claimed in claim 1, wherein the transition metal compound is selected from the group consisting of an inorganic salt, an organic salt, a co-ordination complex and an organometallic complex.

27. The process as claimed in claim 26, wherein the transition metal compound is selected from the group consisting of chromium trichloride tris-tetrahydrofuran complex, (benzene)tricarbonyl chromium, chromium (III) octanoate chromium (III) acetylacetonoate, chromium hexacarbonyl and chromium (III) 2-ethylhexanoate.

28. The process as claimed in claim 27, wherein the transition metal compound is selected from a complex selected from chromium (III) acetylacetonoate and chromium (III) 2-ethylhexanoate.

29. The process as claimed in claim 1, wherein the transition metal compound and the heteroatomic ligand are combined to provide a transition metal/ligand ratio from about 0.01:100 to 10 000:1.

30. The process as claimed in claim 21, wherein the catalyst system further includes an activator selected from the group consisting of an organoaluminium compound, an organoboron compound, an organic salt, an inorganic acid and salt.

31. The process as claimed in claim 30, wherein the activator is an alkylaluminoxane.

32. The process as claimed in claim 31, wherein the transition metal compound and the aluminoxane are combined in proportions to provide an Al/transition metal ratio from about 1:1 to 10 000:1.

33. A tetramerisation catalyst system comprising:
a transition metal compound; and
a heteroatomic ligand described by the following general formula

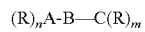

where
A and C are independently an atom selected from the group consisting of phosphorus, arsenic, antimony, oxygen, bismuth, sulphur, selenium and nitrogen or said atom oxidized by S, Se, N or O, where the valance of A and/or C allows for such oxidation;
B is a linking group between A and C;
the R groups are the same or different and each R is independently selected from a homo hydrocarbyl group and a heterohydrocarbyl group, and at least one R has a polar substituent; and
n and m for each R is independently determined by the respective valence and oxidation state of A and C; and
provided that when the heteroatomic ligand is described by the following general formula

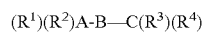

wherein
A and C are independently selected from the group consisting of phosphorus, arsenic, antimony, bismuth and nitrogen;
B is a linking group between A and C; and each of $R^1$, $R^2$, $R^3$ and $R^4$ is independently selected from the group consisting of a non-aromatic group, an aromatic group, and a heteroaromatic group;

at least one of $R^1$, $R^2$, $R^3$ and $R^4$, if aromatic, has a polar substituent on a $2^{nd}$ or further atom from the atom bound to A or C and provided that any polar substituents that $R^1$, $R^2$, $R^3$ and $R^4$ may have, if they are aromatic, are not on the atom adjacent to the atom bound to A or C.

34. The catalyst system as claimed in claim 33, wherein the heteroatomic ligand is described by the following general formula $(R^1)(R^2)A$-B—$C(R^3)(R^4)$ where A and C are independently selected from the group consisting of phosphorus, arsenic, antimony, bismuth, and nitrogen; B is a linking group between A and C; and each of $R^1$, $R^2$, $R^3$ and $R^4$ is independently selected from the group consisting of a non-aromatic group, an aromatic group, and a heteroaromatic group.

35. The catalyst system as claimed in claim 34, wherein each of $R^1$, $R^2$, $R^3$ and $R^4$ is aromatic, including heteroaromatic, but not all of $R^1$, $R^2$, $R^3$ and $R^4$ have a substituent on an atom adjacent to the atom bound to A or C.

36. The catalyst system as claimed in claim 35, wherein not more than two of $R^1$, $R^2$, $R^3$ and $R^4$ have substituents on the atom adjacent to the atom bound to A or C.

37. The catalyst system as claimed in claim 34, wherein each polar substituent that one or more of $R^1$, $R^2$, $R^3$ and $R^4$ may have is electron donating.

38. The catalyst system as claimed in claim 33, wherein A and/or C are a potential electron donor for coordination with the transition metal.

39. The catalyst system as claimed in claim 33, wherein B is selected from the group consisting of an organic linking group comprising a hydrocarbylene, a substituted hydrocarbylene, a hetero hydrocarbylene or a substituted hetero hydrocarbylene; an inorganic linking group comprising a single atom linking spacer; and a group comprising methylene, dimethylmethylene, 1,2-ethylene, 1,2-phenylene, 1,2-propylene, 1,2-catecholate, —$(CH_3)N$—$N(CH_3)$—, —$B(R^5)$—, —$Si(R^5)_2$—, —$P(R^5)$—, or —$N(R^5)$—, where $R^5$ is hydrogen, a hydrocarbyl or substituted hydrocarbyl, a substituted heteroatom or a halogen.

40. The catalyst system as claimed in claim 39, wherein B is a single atom linking spacer.

41. The catalyst system as claimed in claim 39, wherein B is selected to be —$N(R^5)$—, wherein $R^5$ is selected from the groups consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents.

42. The catalyst system as claimed in claim 33, wherein A and/or C is independently oxidised by S, Se, N or O, where the valence of A and/or C allows for such oxidation.

43. The catalyst system as claimed in claim 33, wherein A and C is independently phosphorus or phosphorus oxidised by S or Se or N or O.

44. The catalyst system as claimed in claim 33, wherein the ligand is selected from the group consisting of (3-methoxyphenyl)$_2$PN(methyl)P(3-methoxyphenyl)$_2$, (4-methoxyphenyl)$_2$PN(methyl)P(4-methoxyphenyl)$_2$, (3-methoxyphenyl)$_2$PN(isopropyl)P(3-methoxyphenyl)$_2$, (4-methoxyphenyl)$_2$PN(isopropyl)P(4-methoxyphenyl)$_2$, (4-methoxyphenyl)$_2$PN(2-ethylhexyl)P(4-methoxyphenyl)$_2$, (3-methoxyphenyl)(phenyl)PN(methyl)P(phenyl)$_2$ and (4-methoxyphenyl)(phenyl)PN(methyl)P(phenyl)$_2$, (3-methoxyphenyl)(phenyl)PN(methyl)P(3-methoxyphenyl)(phenyl), (4-methoxyphenyl)(phenyl)PN(methyl)P(4-methoxyphenyl)(phenyl), (3-methoxyphenyl)$_2$PN(methyl)P(phenyl)2 and (4-methoxyphenyl)$_2$PN(methyl)P(phenyl)$_2$, (4-methoxyphenyl)$_2$PN(1-cyclohexylethyl)P(4-methoxyphenyl)$_2$, (4-methoxyphenyl)$_2$PN (2-methylcyclohexyl)P(4-methoxyphenyl)$_2$, (4-methoxyphenyl)$_2$PN (decyl)P(4-methoxyphenyl)$_2$, (4-methoxyphenyl)$_2$PN(pentyl)P(4-methoxyphenyl)$_2$, (4-methoxyphenyl)$_2$PN(benzyl)P(4-methoxyphenyl)$_2$, (4-methoxyphenyl)$_2$PN(phenyl)P(4-methoxyphenyl)$_2$, (4-fluorophenyl)$_2$PN(methyl)P(4-fluorophenyl)$_2$, (3-fluorophenyl)$_2$PN(methyl)P(3-fluorophenyl)$_2$, (4-dimethylamino-phenyl)$_2$PN(methyl)P(4-dimethylamino-phenyl)$_2$, (4-methoxyphenyl)$_2$PN (allyl)P(4-methoxyphenyl)$_2$, (4-(4-methoxyphenyl)-phenyl)$_2$PN(isopropyl)P(4-(4-methoxyphenyl)-phenyl)$_2$, and (4-methoxyphenyl)(phenyl)PN(isopropyl)P(phenyl)$_2$.

45. The catalyst system as claimed in claim 33, wherein the transition metal in the transition metal compound is selected from the group consisting of chromium, molybdenum, tungsten, titanium, tantalum, vanadium and zirconium.

46. The catalyst system as claimed in claim 45, wherein the transition metal is chromium.

47. The catalyst system as claimed in claim 33, wherein the transition metal compound is selected from the group consisting of an inorganic salt, an organic salt, a co-ordination complex and an organometallic complex.

48. The catalyst system as claimed in claim 47, wherein the transition metal compound is selected from the group consisting of chromium trichloride tris-tetrahydrofuran complex, (benzene)tricarbonyl chromium, chromium (III) octanoate, chromium (III) acetylacetonoate, chromium hexacarbonyl, and chromium (III) 2-ethylhexanoate.

49. The catalyst system as claimed in claim 48, wherein the transition metal is selected from a complex selected from chromium (III) acetylacetonoate and chromium (III) 2-ethylhexanoate.

50. The catalyst system as claimed in claim 33, wherein the transition metal compound and the heteroatomic ligand are combined to provide a transition metal/ligand ratio from about 0.01:100 to 10000:1.

51. The catalyst system as claimed in claim 33, which further includes an activator.

52. The catalyst system as claimed in claim 51, wherein the activator is selected from the group consisting of an organoaluminium compound, an organoboron compound, an organic salt, an inorganic acid and salt.

53. The catalyst system as claimed in claim 52, wherein the activator is an alkylaluminoxane.

54. The catalyst system as claimed in claim 53, wherein the alkylaluminoxane is selected from the group consisting of methylaluminoxane (MAO), ethylaluminoxane (EAO) modified alkylaluminoxanes (MMAO), and mixtures thereof.

55. The catalyst system as claimed in claim 53, wherein the transition metal and the aluminoxane are combined in proportions to provide an Al/transition metal ratio from about 1:1 to 10000:1.

56. The process of claim 30, wherein the activator is methyllithium, methylmagnesium bromide, tetrafluoroboric acid diethylether complex, silver tetrafluoroborate or sodium hexafluoroantimonate.

57. The process of claim 52, wherein the activator is methyllithium, methylmagnesium bromide, tetrafluoroboric acid diethylether complex, silver tetrafluoroborate or sodium hexafluoroantimonate.

* * * * *

UNITED STATES PATENT AND TRADEMARK OFFICE
CERTIFICATE OF CORRECTION

PATENT NO. : 7,297,832 B2
APPLICATION NO. : 10/539237
DATED : November 20, 2007
INVENTOR(S) : Kevin Blann et al.

It is certified that error appears in the above-identified patent and that said Letters Patent is hereby corrected as shown below:

In claim 10, column 22, line 55, "C8:C6" should read --$C_8:C_6$--.

In claim 20, column 23, lines 36-38, "(4-methoxyphenyl)$_2$PN(methyl)P(4-methoxyphenyl)$_2$(3-methoxyphenyl)$_2$PN(isopropyl)P(3-methoxyphenyl)$_2$," should read --(4-methoxyphenyl)$_2$PN(methyl)P(4-methoxyphenyl)$_2$, (3-methoxyphenyl)$_2$PN(isopropyl)P(3-methoxyphenyl)$_2$,--.

In claim 44, column 26, line 2, "(3-methoxyphenyl)$_2$PN(methyl)P(phenyl)2" should read --(3-methoxyphenyl)$_2$PN(methyl)P(phenyl)$_2$--.

Signed and Sealed this

Seventh Day of October, 2008

JON W. DUDAS
*Director of the United States Patent and Trademark Office*